US008512357B2

(12) United States Patent
Viola

(10) Patent No.: US 8,512,357 B2
(45) Date of Patent: Aug. 20, 2013

(54) SURGICAL CLIP APPLIER WITH HIGH TORQUE JAWS

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 1661 days.

(21) Appl. No.: 10/510,165

(22) PCT Filed: Apr. 3, 2003

(86) PCT No.: PCT/US03/10231
§ 371 (c)(1),
(2), (4) Date: Oct. 1, 2004

(87) PCT Pub. No.: WO03/086207
PCT Pub. Date: Oct. 23, 2003

(65) Prior Publication Data
US 2005/0177177 A1    Aug. 11, 2005

Related U.S. Application Data

(60) Provisional application No. 60/371,652, filed on Apr. 10, 2002.

(51) Int. Cl.
*A61B 17/10* (2006.01)
(52) U.S. Cl.
USPC .......................................................... 606/142
(58) Field of Classification Search
USPC ................ 606/139, 142, 143, 151, 157, 158, 606/205, 207, 210, 219, 206; 227/175.1; 81/112
See application file for complete search history.

(56) References Cited

U.S. PATENT DOCUMENTS

| 1,482,290 | A |   | 1/1924 | Elzi |
| 2,585,098 | A | * | 2/1952 | Elliott ............................. 81/112 |
| 3,140,715 | A | * | 7/1964 | Whitton, Jr. et al. ......... 606/210 |
| 3,363,628 | A | * | 1/1968 | Wood ............................ 606/158 |
| 3,631,707 | A |   | 1/1972 | Miller |

(Continued)

FOREIGN PATENT DOCUMENTS

| EP | 0 085 931 A2 | 8/1983 |
| EP | 0 324 166 A2 | 7/1989 |

(Continued)

OTHER PUBLICATIONS

International Search Report from PCT/US03/10231.

(Continued)

*Primary Examiner* — Julian Woo

(57) ABSTRACT

Jaw blades for use in surgical clip appliers are disclosed. The jaw blades include a first leg and a second leg, each leg having a jaw integrally connected thereto and at least one inter-leg engaging member that extends from one of the first and second legs and is engageable with the other of the first and second legs. When the at least one inter-leg engaging member is engaged with the other of the first and second legs, a displacement in a first direction of one of the first and second legs causes a first corresponding displacement in the first direction of the other of the first and second legs, and such that a displacement in a second direction, opposite the first direction, of the one of the first and second legs causes a second corresponding displacement in the second direction of the other of the first and second legs.

30 Claims, 10 Drawing Sheets

(56) References Cited

U.S. PATENT DOCUMENTS

| | | | |
|---|---|---|---|
| 3,646,801 A * | 3/1972 | Caroli | 606/143 |
| 3,653,389 A * | 4/1972 | Shannon | 606/210 |
| 4,166,466 A * | 9/1979 | Jarvik | 606/143 |
| 4,212,305 A * | 7/1980 | Lahay | 606/210 |
| 4,318,313 A * | 3/1982 | Tartaglia | 606/207 |
| 4,452,106 A * | 6/1984 | Tartaglia | 606/210 |
| 4,452,376 A | 6/1984 | Klieman et al. | |
| 4,491,133 A | 1/1985 | Menges et al. | |
| 4,512,345 A * | 4/1985 | Green | 606/143 |
| 4,534,351 A | 8/1985 | Rothfuss et al. | |
| 4,549,544 A | 10/1985 | Favaron | |
| 4,572,183 A | 2/1986 | Juska | |
| 4,576,166 A | 3/1986 | Montgomery et al. | |
| 4,598,711 A | 7/1986 | Deniega | |
| 4,611,595 A | 9/1986 | Klieman et al. | |
| 4,646,740 A | 3/1987 | Peters et al. | |
| 4,648,401 A | 3/1987 | Mattson | |
| 4,662,373 A | 5/1987 | Montgomery et al. | |
| 4,667,671 A | 5/1987 | Danzig | |
| 4,669,470 A | 6/1987 | Brandfield | |
| 4,674,504 A | 6/1987 | Klieman et al. | |
| 4,712,549 A | 12/1987 | Peters et al. | |
| 4,850,355 A | 7/1989 | Brooks et al. | |
| 4,924,864 A | 5/1990 | Danzig | |
| 5,019,091 A * | 5/1991 | Porat et al. | 606/205 |
| 5,047,038 A | 9/1991 | Peters et al. | |
| 5,049,152 A | 9/1991 | Simon et al. | |
| 5,104,394 A | 4/1992 | Knoepfler | |
| 5,104,395 A | 4/1992 | Thornton et al. | |
| 5,112,343 A | 5/1992 | Thornton | |
| 5,156,431 A * | 10/1992 | Lowe | 606/210 |
| 5,163,945 A | 11/1992 | Ortiz et al. | |
| 5,171,247 A | 12/1992 | Hughett et al. | |
| 5,171,249 A | 12/1992 | Stefanchik et al. | |
| 5,199,566 A | 4/1993 | Ortiz et al. | |
| 5,207,691 A | 5/1993 | Nardella | |
| 5,236,437 A * | 8/1993 | Wilk et al. | 606/207 |
| 5,246,450 A | 9/1993 | Thornton et al. | |
| 5,282,807 A | 2/1994 | Knoepfler | |
| 5,290,299 A | 3/1994 | Fain et al. | |
| 5,330,487 A | 7/1994 | Thornton et al. | |
| 5,366,458 A * | 11/1994 | Korthoff et al. | 606/151 |
| 5,382,253 A | 1/1995 | Hogendijk | |
| 5,403,327 A | 4/1995 | Thornton et al. | |
| 5,409,498 A | 4/1995 | Braddock et al. | |
| 5,415,666 A | 5/1995 | Gourlay et al. | |
| 5,431,668 A | 7/1995 | Burbank, III et al. | |
| 5,447,513 A | 9/1995 | Davison et al. | |
| 5,486,185 A | 1/1996 | Freitas et al. | |
| 5,522,823 A | 6/1996 | Kuntz et al. | |
| 5,527,320 A | 6/1996 | Carruthers et al. | |
| 5,542,949 A | 8/1996 | Yoon | |
| 5,601,573 A | 2/1997 | Fogelberg et al. | |
| 5,626,586 A | 5/1997 | Pistl et al. | |
| 5,632,751 A | 5/1997 | Piraka | |
| RE35,525 E | 6/1997 | Stefanchik et al. | |
| 5,634,932 A | 6/1997 | Schmidt | |
| 5,769,303 A | 6/1998 | Knodel et al. | |
| 5,769,857 A | 6/1998 | Reztzov et al. | |
| 5,779,131 A | 7/1998 | Knodel et al. | |
| 5,779,132 A | 7/1998 | Knodel et al. | |
| 5,779,718 A | 7/1998 | Green et al. | |
| 5,797,922 A | 8/1998 | Hessel et al. | |
| 5,797,958 A | 8/1998 | Yoon | |
| 5,904,693 A | 5/1999 | Dicesare et al. | |
| 5,984,939 A | 11/1999 | Yoon | |
| 5,993,465 A | 11/1999 | Shipp et al. | |
| 6,013,088 A | 1/2000 | Karavidas | |
| 6,019,758 A | 2/2000 | Slater | |
| 6,066,174 A * | 5/2000 | Farris | 606/206 |
| 6,241,740 B1 | 6/2001 | Davis et al. | |
| 6,277,131 B1 | 8/2001 | Kalikow | |
| 6,319,257 B1 * | 11/2001 | Carignan et al. | 606/205 |
| 6,423,079 B1 | 7/2002 | Blake, III | |
| 6,923,818 B2 | 8/2005 | Muramatsu et al. | |
| 6,991,635 B2 | 1/2006 | Takamoto et al. | |
| 2003/0009193 A1 | 1/2003 | Corsaro | |
| 2005/0288690 A1 | 12/2005 | Bourque et al. | |
| 2006/0004388 A1 | 1/2006 | Whayne et al. | |
| 2006/0009789 A1 | 1/2006 | Gambale et al. | |
| 2006/0009792 A1 | 1/2006 | Baker et al. | |
| 2006/0020270 A1 | 1/2006 | Jabba et al. | |
| 2006/0064117 A1 | 3/2006 | Aranyi et al. | |
| 2006/0079913 A1 | 4/2006 | Whitfield et al. | |
| 2006/0085015 A1 | 4/2006 | Whitfield et al. | |
| 2006/0235444 A1 | 10/2006 | Huitema et al. | |

FOREIGN PATENT DOCUMENTS

| | | |
|---|---|---|
| EP | 0 392 750 A1 | 10/1990 |
| EP | 0 732 078 A2 | 9/1996 |
| EP | 0 755 655 A | 1/1997 |
| EP | 1 609 427 A1 | 12/2005 |
| EP | 1 712 191 A2 | 10/2006 |
| EP | 1 813 199 A1 | 8/2007 |
| EP | 1 908 423 A | 4/2008 |
| EP | 1 913 881 A1 | 4/2008 |
| WO | WO 2008/118928 A2 | 10/2008 |
| WO | WO 2008/127968 A | 10/2008 |

OTHER PUBLICATIONS

European Search Report corresponding to EP 09252053; date of mailing is Dec. 1, 2009; date of completion of Search is Nov. 24, 2009 (3 Pages).

European Search Report corresponding to EP 09252051; date of mailing is Jan. 28, 2010; date of completion of Search is Dec. 21, 2009 (3 Pages).

European Search Report corresponding to EP 09252050; date of mailing is Jan. 21, 2010; date of completion of Search is Dec. 23, 2009 (3 Pages).

European Search Report corresponding to EP 09252054; date of mailing is Jan. 22, 2010; date of completion of Search is Jan. 7, 2010 (3 Pages).

Extended European Search Report corresponding to EP 09252056.8, date of mailing is Feb. 5, 2010; date of completion of Search is Jan. 8, 2010 (3 Pages).

Extended European Search Report corresponding to EP 10250497.4, date of mailing is May 12, 2010; date of completion of Search is May 4, 2010 (6 Pages).

Extended European Search Report corresponding to EP 10252079.8, date of mailing is Mar. 17, 2011; date of completing of Search is Mar. 8, 2011 (3 Pages).

* cited by examiner

US 8,512,357 B2

SURGICAL CLIP APPLIER WITH HIGH TORQUE JAWS

CROSS-REFERENCE TO RELATED APPLICATIONS

This application is a National Stage Application of PCT/US03/10231 filed on Apr. 3, 2003 under 35 USC §371 (a), which claims priority of U.S. Provisional Patent Application Ser. No. 60/371,652 filed Apr. 10, 2002, the disclosures of each of the above-identified applications are hereby incorporated by reference in their entirety.

BACKGROUND

1. Technical Field

The present disclosure relates to an apparatus for applying surgical clips to body tissue during open, laparoscopic or endoscopic procedures and, more particularly, to a surgical clip applier having jaws configured and adapted to withstand torsional forces acting thereon.

2. Background of Related Art

In laparoscopic and endoscopic surgical procedures, a small incision is made in the patient's body to provide access for a cannula device. Once extended into the patient's body, the cannula provides an access port which allows insertion of various surgical instruments, through the cannula, for acting on organs, blood vessels, ducts or body tissue that can be far removed from the incision. In many instances, several small incisions must be made in the patient's body in order to provide access of several instruments into the patient's body. Undoubtably, the more incisions required, the greater the trauma inflicted on the patient's body.

In surgical procedures, it is often necessary or desirable for a surgeon to grasp and/or blunt dissect in conjunction with applying surgical clips to a target area. Often, this requires the surgeon to make two incisions, one for the blunt dissection instrument and one for the endoscopic applier. However, recently, in order to reduce the trauma inflicted on the patient's body, surgeons have begun to perform blunt dissections using the distal end of an endoscopic fastener or clip applier in order to perform the blunt dissection itself. In so doing, the surgeon eliminates the need to make extra incisions or to repeatedly, alternately insert the clip applier and then the blunt dissector.

When performing a blunt dissection, the distal end of a dissection instrument is used to separate or divide tissue by dividing the interconnecting membrane through repeated twisting and/or separating actions. For example, if the distal end of a surgical fastener or clip applier instrument with jaws were to be used for blunt dissection, the distal end of the jaws would be pressed into the interconnecting membrane and the jaws would then be opened and/or twisted, which opening and/or twisting would separate the interconnecting membrane. The procedure might be repeated as often as needed in order to fully separate the adjacent corporal bodies.

Thus, the need exists for a surgical fastener or clip applier and, more particularly, to a jaw mechanism for a surgical fastener or clip applier which is configured and adapted to withstand torsional forces acting at least on a distal end thereof.

SUMMARY

The present disclosure is directed to an apparatus for applying surgical fasteners or clips to body tissue during open, laparoscopic or endoscopic procedures having jaws configured and adapted to withstand torsional forces acting thereon.

According to a first aspect of the present disclosure, a jaw blade for use in a surgical clip applier, including a first leg and a second leg, each leg having a jaw integrally connected thereto, and at least one inter-leg engaging member that extends from one of the first and second legs and is engageable with the other of the first and second legs is disclosed.

Preferably, when the at least one inter-leg engaging member is engaged with the other of the first and second legs, a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

According to one embodiment, the jaw blade includes two inter-leg engaging members, a first inter-leg engaging member that extends from the first leg and is engageable with the second leg, and a second inter-leg engaging member that extends from the second leg and is engageable with the first leg. Preferably, when the respective first and second inter-leg engaging members are engaged with the respective second and first legs, a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

It is envisioned that the first inter-leg engaging member includes a first arm configured and adapted to engage the second leg, and the second inter-leg engaging member includes a second arm configured and adapted to engage the first leg.

In another embodiment, it is envisioned that the first leg includes an inner surface oriented toward the second leg and a recess formed in an upper portion of the inner surface of the first leg, and the second leg includes an inner surface oriented toward the first leg and a recess formed in an upper portion of the inner surface of the second leg, the inner surface of the first leg having a first inter-leg engaging member comprised of a first arm that includes a tongue extending distally therefrom, the tongue of the first arm being configured and dimensioned to be received in and being engageable with the recess in the upper portion of the second leg, and the inner surface of the second leg having a second inter-leg engaging member comprised of a second arm that includes a tongue extending distally therefrom, the tongue extending from the second arm being configured and dimensioned to be received in and being engageable with the recess in the upper portion of the first leg.

In yet another embodiment, it is envisioned that there are two inter-leg engaging members, a first inter-leg engaging member including a first arm that extends from the first leg and closely overlies and is engageable with the second leg, and a second inter-leg engaging member including a second arm that extends from the first leg and closely underlies and is engageable with the second leg.

In a further embodiment, it is envisioned that the first leg includes a first arm that extends from the first leg toward the second leg, the first arm including a pair of spaced apart tongues extending distally therefrom, the second leg including an upper and lower surface, wherein an upper recess is formed in the upper surface thereof, and a lower recess is formed in the lower surface thereof, wherein the pair of spaced apart tongues of the first arm are configured and dimensioned to be received in and be engageable with the upper and lower recesses formed respectively in the upper and lower surfaces of the second leg. Preferably, the pair of spaced apart tongues of the first arm closely overlie and underlie the respective upper and lower recesses of the second leg.

It is contemplated that when the jaw blade is assembled in a surgical clip applier and the jaws of the jaw blade are in an open position, a portion of the inter-leg engaging member that extends from one of the first and second legs, closely overlies a portion of the other of the first and second legs.

It is envisioned that a portion of the tongue of the first arm closely overlies the recess in the second upper surface of the second leg, and a portion of the tongue of the second arm closely underlies the recess in the first lower surface of the first leg.

It is envisioned that each of the first and second legs includes a neck adjacent the jaw of the respective first and second legs, and the inter-leg engaging member extends from one of the necks. Preferably, there are two inter-leg engaging members, one that extends from the neck of the first leg, and another that extends from the neck of the second leg.

According to another aspect of the disclosure, a jaw blade for use in a surgical clip applier includes a first leg and a second leg, each leg having a jaw integrally connected thereto, and at least one inter-leg engaging member that extends from one of the first and second legs, and extends between and is engaged with the other of the first and second legs. It is envisioned that when the at least one inter-leg engaging member is slidingly engaged with the other of the first and second legs, such that a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

Preferably, the first leg includes a first neck portion and the second leg includes a second neck portion, the first and second neck portions adjoining the first and second jaws. The at least one inter-leg engaging member includes a first arm that extends from the first neck portion and slidingly engages the second neck portion, and a second arm, spaced from the first arm, that extends from the second neck portion and slidingly engages the first neck portion.

The first neck portion includes a first inner surface oriented toward the second neck portion and a recess formed in a lower portion of the first inner surface, and the second neck portion includes a second inner surface oriented toward the first neck portion and a recess formed in a lower portion of the second inner surface, the first arm extending from the first inner surface of the first neck portion and includes a tongue extending distally therefrom, the tongue extending from the arm being configured and adapted to be received in the recess formed in the lower portion of the second neck portion, and the second arm extending from the second inner surface of the second neck portion and includes a tongue extending distally therefrom, the tongue extending from the second arm being configured and adapted to be received in the recess formed in the lower portion of the first neck portion, at least one of the first and second tongues being slidingly engaged with its respective recess.

The at least one inter-leg engaging member can include a first arm configured and adapted to extend from the first neck portion and overlie and slidingly engage the second neck portion, and a second arm configured and adapted to extend from the second neck portion and overlie and slidingly engage the first neck portion.

The at least one inter-leg engaging member includes a first arm configured and adapted to extend from the first neck portion and overlie and slidingly engage the second neck portion, and a second arm configured and adapted to extend from the first neck portion and underlie and slidingly engage the second neck portion.

It is contemplated that the jaw blade defines a longitudinal axis, and wherein the first neck portion includes an arm extending from the first neck portion substantially toward the second neck portion, the arm including a pair of spaced apart tongues extending at an angle to the longitudinal axis of the jaw blade, wherein the second neck portion includes a recess formed in each of the upper and lower surface thereof, and wherein the pair of spaced apart tongues of the arm respectively slidingly engage the recesses formed in the upper and lower surfaces of the second neck portion.

According to another aspect of the present disclosure, in an apparatus for applying surgical fasteners or clips, wherein the apparatus including a handle portion, a body portion extending from the handle portion, a jaw mechanism extending from the body portion at an end opposite the handle portion and having a first leg and a second leg, each leg having a jaw integrally connected thereto, the jaw mechanisms being movable between an open position for receiving a fastener or clip and a closed position for forming the fastener or clip in response to a movement of the handle portion, and a fastener or clip supply disposed within the body portion, the improvement in the jaw mechanism includes at least one inter-leg engaging member extending between and being adapted to effect an engagement between the first and second legs, wherein vertical displacement in a first direction of one of the first and second legs causes a corresponding displacement in the first direction of the other of the first and second legs, and wherein a vertical displacement in a second direction, opposite the first direction, of one of the first and second legs causes a second corresponding displacement in the second direction of the other of the first and second legs.

Preferably, the at least one inter-leg engaging member is adapted to effect engagement when the jaws are in an open position. The at least one inter-leg engaging member is adapted to effect engagement when the jaws are in a closed position.

In a further aspect of the present disclosure, a jaw blade for use in a surgical clip applier, including a first leg, a second leg spaced from and parallel to the first leg, the first and second legs defining a plane, each leg including a jaw integrally formed at a distal end thereof, and at least one inter-leg engaging member extending between the first and the second legs and operatively engaged therewith, wherein the inter-leg engaging member maintains or reduces the loss of co-planarity of the first leg with respect to the second leg. It is envisioned that the the operative engagement of at least one inter-leg engaging member causes the first and second leg members to deflect and maintain their co-planarity when one of the first and second legs is deflected in a direction which is orthogonal with respect to the plane defined by the first and second legs.

According to a first embodiment, the jaw blade includes a first inter-leg engaging member integrally formed with the first leg and extending substantially toward the second leg, the first inter-leg engaging member including a tongue extending from a distal end thereof, which tongue is configured and dimensioned to interengage a recess formed in a surface of the second leg, and a second inter-leg engaging member integrally formed with the second leg and extending substantially toward the first leg, the second leg inter-engaging member including a tongue extending from a distal end thereof, which tongue is configured and dimensioned to interengage a recess formed in a surface of the first leg.

Preferably, the recess formed in the second leg is formed in one of a top and a bottom surface thereof, and wherein the recess formed in the first leg is formed in one of a top and a bottom surface thereof, which recess formed in the first leg is formed in the surface opposite the top and bottom surface in which the recess of the second leg is formed.

According to an alternate embodiment, the jaw blade includes a single inter-leg engaging member integrally formed with one of the first and second legs and extending substantially toward the other of the first and second legs, the inter-leg engaging member including a pair of tongues extending from a distal end of the inter-leg engaging member and spaced from one another in a direction orthogonal to the plane defined by the first and second legs, each tongue of the pair of tongues being configured and dimensioned to interengage a respective recess formed in a top surface and a bottom surface of the second leg.

The present disclosure is also directed to a method for applying surgical clips and performing blunt dissection of tissue. The method including the steps of providing a surgical clip applier, and applying a surgical clip to a tissue or vascular target area utilizing the clip applier. The surgical clip applier includes a jaw blade having a first leg and a second leg, each of the first and second legs having a jaw integrally connected thereto, and at least one inter-leg engaging member extending between and effecting an engagement between the first and second legs, such that a vertical displacement in a first direction of one of the first and second legs causes a first corresponding displacement in the first direction of the other of the first and second legs, and such that a vertical displacement in a second direction, opposite the first direction, of one of the first and second legs causes a second corresponding displacement in the second direction of the other of the first and second legs, performing a blunt dissection technique utilizing the jaws of the clip applier.

It is an object of the present disclosure to provide an apparatus for applying surgical fasteners or clips to body tissue during open, laparoscopic or endoscopic procedures.

It is another object of the present disclosure to provide an apparatus for applying a surgical fastener or clip that is used to manipulate and/or blunt dissect tissue prior or subsequent to applying fasteners or clips.

Another object of the present disclosure is to provide an apparatus for applying surgical fasteners or clips which has increased resistance to the loading (e.g., torsional, twisting, bending, etc.) effects experienced during grasping, manipulating and blunt dissecting techniques.

Another object of the present disclosure is to provide an apparatus for applying surgical fasteners or clips having a jaw configuration which is inherently resistant to distortion due to manipulation during grasping and blunt dissecting techniques.

A further object of the present disclosure is to provide a surgical fastener or clip applier that is easier to load with a fastener or clip and which makes forming the same easier.

A further object of the present disclosure is to provide an apparatus having coplanar jaws for applying a surgical clip, which jaws maintain their coplanarity.

A further object of the invention is to provide a surgical fastener or clip applier that has increased resistance to torsional forces and properly loads, forms and applies surgical fasteners or clips after having performed a blunt dissection procedure.

These objects together with other objects of the disclosure, along with the various features of novelty which characterize the disclosure, are pointed out with particularity in the claims annexed to and forming a part of this disclosure.

BRIEF DESCRIPTION OF THE DRAWINGS

By way of example only, preferred embodiments of the disclosure will be described with reference to the accompanying drawings, in which.

DETAILED DESCRIPTION OF PREFERRED EMBODIMENTS

Figure 1:
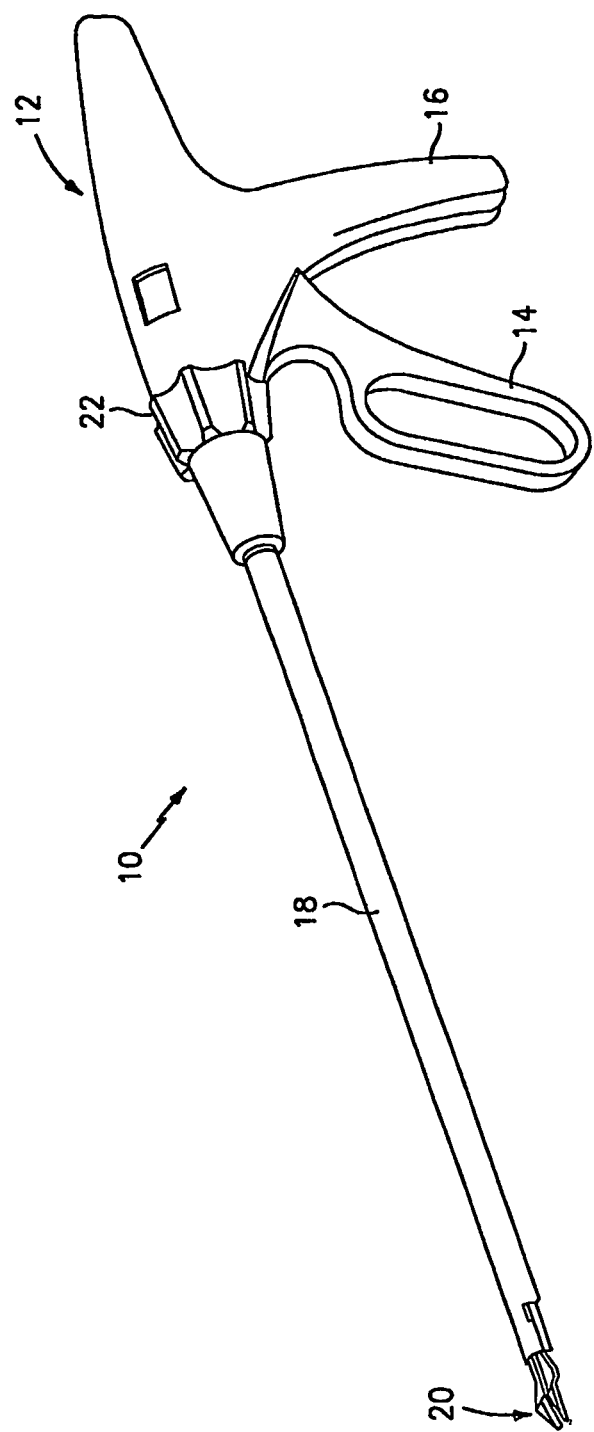
FIG. 1 is a perspective view of a prior art apparatus for applying surgical clips in laparoscopic or endoscopic procedures.

Preferred embodiments of the presently disclosed endoscopic applier having high torque jaws will now be described in detail with reference to the drawing figures wherein like reference numerals identify similar or identical elements. In the drawings and in the description which follows, the term "proximal", as is traditional will refer to the end of the surgical applier which is closest to the operator, while the term "distal" will refer to the end of the applier which is furthest from the operator.

Referring now in detail to the figures, in which like reference numerals identify similar or identical elements, FIG. 1 illustrates a typical prior art surgical fastener or clip applying apparatus, here shown as surgical clip applier 10. Clip applier 10 includes a handle portion 12 having a movable handle 14 and a stationary hand grip 16, which handle portion 12 serves to operate a jaw mechanism 20 through the provision of an elongated body portion 18. For example only, the junction at which the body portion 18 is joined to the handle portion 12 includes a rotation collar 22 for varying the orientation of the jaw mechanism 20 at the surgical site. Typical surgical clip applying instruments are described in commonly assigned U.S. Pat. No. 5,607,436 to Pratt et al. and U.S. Pat. No. 5,084,057 to Green et al., the entire disclosures of which are incorporated herein by reference.

Figure 2:
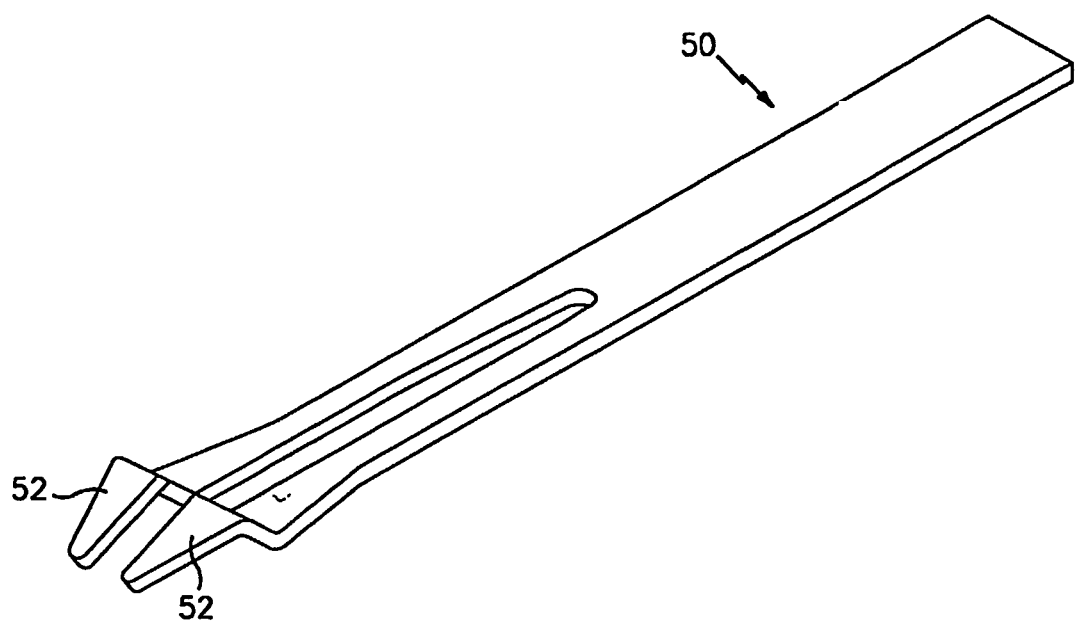
FIG. 2 is an enlarged perspective view of the jaw mechanism for the apparatus of FIG. 1.

FIG. 2 shows a jaw mechanism in the form of an integral jaw blade, generally 50, which at a distal end has a pair of coplanar jaws 52 in an open position for reception of a surgical clip therein. The basic objective of the jaw blade 50 is to bias surgical clips (not shown), after the jaws themselves have been positioned around an artery or blood vessel, by closing the jaws together thereby bringing together portions of the legs of a "U" or other appropriately shaped clips in order to sufficiently close the artery or blood vessel. Jaw blade 50 is preferably fabricated in one piece and preferably of a material having sufficient resilience such that clamping of jaws 52 toward each other to close a clip therebetween will be followed by a return of the jaws to their original position upon release of the clamping forces. Such a material can include, for example, a suitable metal, thermoplastic or thermoset or a combination thereof. It is understood that jaw blade 50 can include legs or members that are not monolithically formed, and that the legs need not be joined together at their proximal ends.

In a clamping procedure, jaws 52 are closed by the clamping forces imposed for example by distal movement of a tubular or other suitable member over the jaws. However, since each jaw 52 is located at the distal end of the blade 50 and is essentially independent of the other jaw, in a blunt dissection procedure using partly or fully opened or closed jaws, vertical or other deflection forces, e.g., a torsional force (i.e., a twisting force) and/or a bending force may be applied to the distal end of one or both jaws 52 or legs.

As described in greater detail below, these deflection forces acting on each leg, whether the jaws are in an open or closed position, tend to cause the legs of the jaw blade to create a torque or a twisting about the longitudinal axis of the jaw blade. These forces can cause the legs and/or jaws of the jaw blade to come out of alignment and/or co-planarity with one another. Turning now to the remainder of the figures, jaw blades, in accordance with the present disclosure, having one or more inter-leg engaging members providing one or more inter-leg engaging or engagable surfaces for reducing the effects of vertical deflection forces acting on each leg of the jaw blade are disclosed.

Figure 3:
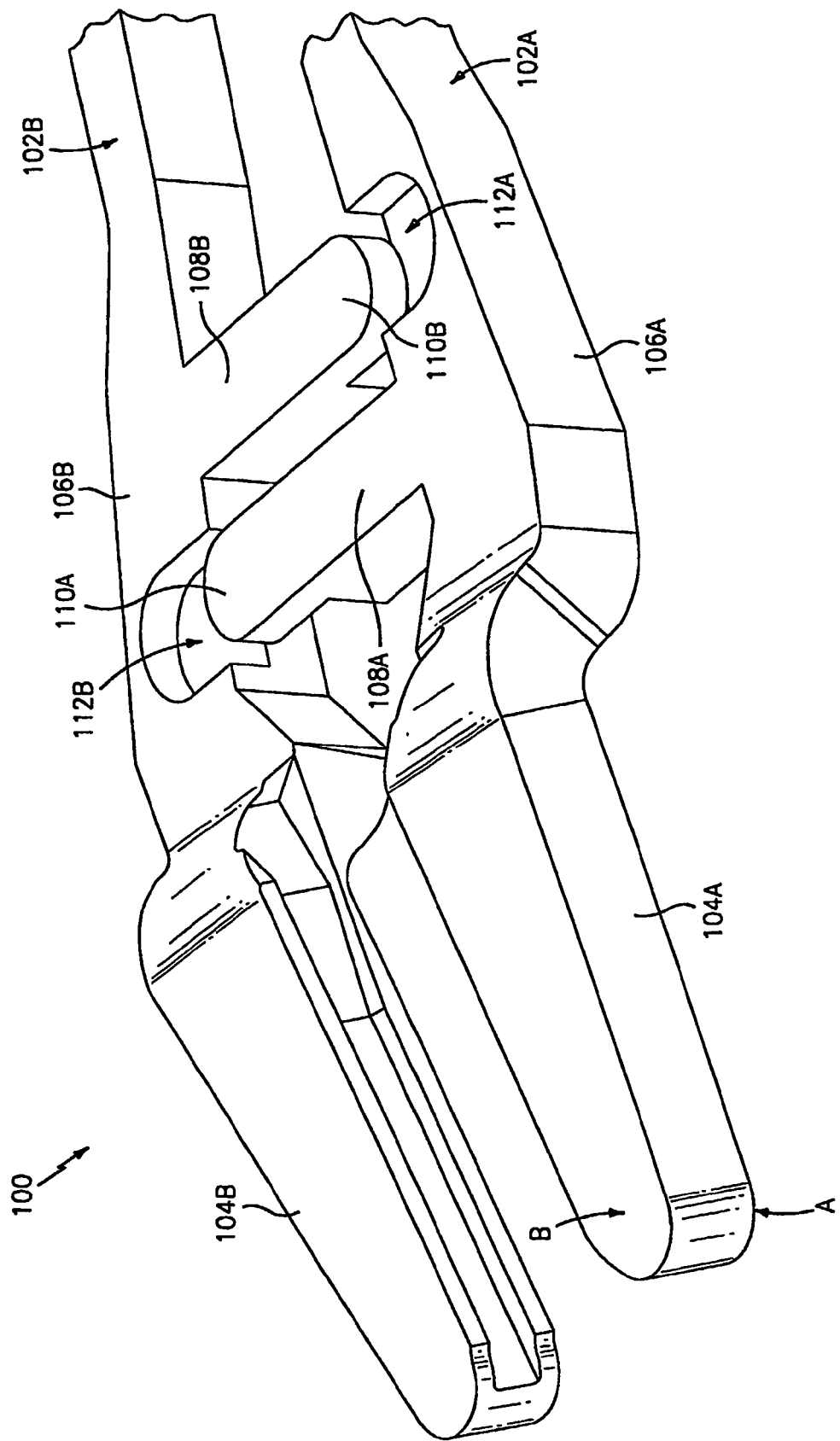
FIG. 3 is an enlarged perspective view, with portions broken away, of a distal end of a jaw mechanism according to the present disclosure.
Figure 3A:
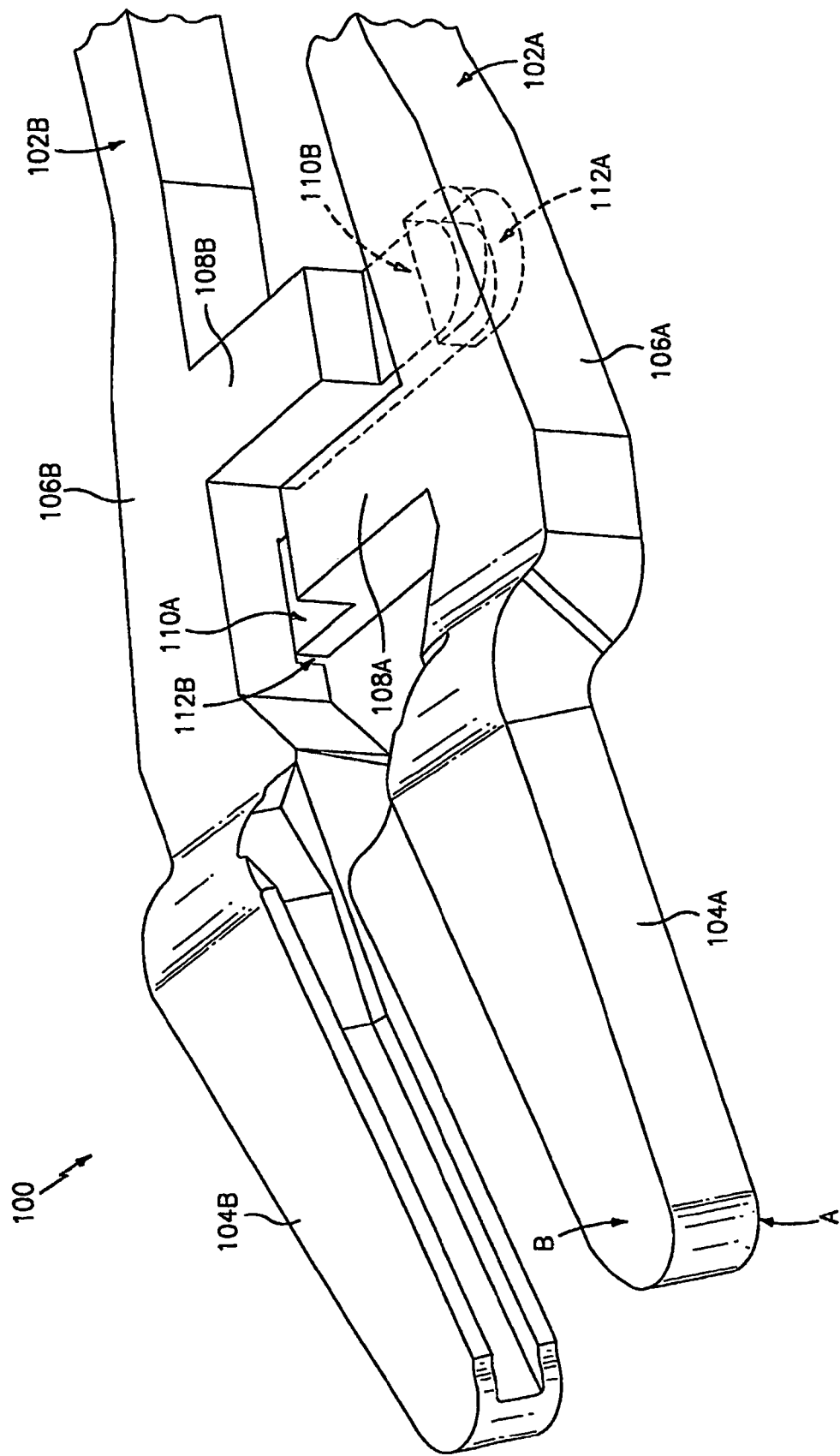
FIG. 3A is an enlarged perspective view, with portions broken away, of the distal end of a jaw mechanism of FIG. 3, illustrating an alternative construction thereof.

FIG. 3 shows the distal end portion of a jaw blade, generally designated 100, in accordance with the present disclosure for use in connection with a surgical clip applying instrument, for example, clip applier 10. Jaw blade 100 includes a first leg and a second leg, 102A and 102B, respectively, each having a corresponding intermediate neck portion 106A and 106B, and a corresponding jaw 104A and 104B formed at a distal end of a respective leg and configured and adapted for receiving a surgical clip (not shown) therebetween. Preferably, legs 102A, 102B are co-planar and together define a plane. Jaw blade 100 further includes inter-leg engaging members preferably comprised of a pair of arms 108A and 108B axially spaced from one another and preferably extending from and between the inner surfaces of each respective neck portion 106A, 106B (i.e., the surfaces of each respective neck portion which are oriented toward and substantially face one another) of jaw blade 100. Each arm 108A and 108B includes a tongue 110A and 110B extending from the main portion of the arm. Tongues 110A and 110B are configured and adapted to engage or be engageable with a corresponding recess 112A and 112B formed in a suitable surface, preferably in a top surface (or, alternatively in a bottom surface as seen in FIG. 3A) of respective neck portions 106A and 106B at least when jaws 104A, 104B are in an assembled, less than full open position. Preferably, at least a portion of each tongue closely overlies a portion of a recess at least when the assembled jaws are fully open.

Further, as seen in FIG. 3, by way of example only, the ends of tongues 110A and 110B, at the distal ends of arms 108A, 108B, preferably are generally U-shaped and sized to be received in and mate with corresponding or complementary U-shaped recesses 112A and 112B. While generally "U" shaped tongues and recesses are shown, it is envisioned that any configuration and/or shape of tongue and recess can be provided. For example, the tongue need not be horizontally disposed but can be a vertical beam that extends from one neck portion and which fits snuggly into a vertical recess formed in a corresponding surface of an opposite neck portion. The tongues and/or arms need not be identical, and the same applies to the recesses.

In a blunt dissecting technique performed with a clip applier 10 having a jaw blade 100 according to the present disclosure, with no surgical clip in place, i.e., when jaws 104A, 104B are open, when a deflecting force is applied in a direction "A" on the first jaw 104A, which force "A" tends to cause jaw 104A to deflect in a direction orthogonal to the plane defined by legs 102A, 102B, thereby causing the pair of jaws 104A and 104B to twist or bend about one another in a counter-clockwise direction and to become out of plane with one another, the floor of recess 112A formed in neck 106A will engage or abut against the corresponding juxtaposed surface of tongue 110B projecting from the corresponding arm 108B extending from second neck 106B, thereby preventing first jaw 104A from twisting about second jaw 104B and become out of plane with one another. Likewise, when a force is applied in a direction "B", opposite to the direction "A", on the first jaw 104A, which force "B" tends to cause jaw 104A to deflect in a direction orthogonal to the plane defined by legs 102A, 102B, thereby causing the pair of jaws 104A and 104B to twist about one another in a clockwise direction and become out of plane with one another, tongue 110A projecting from arm 108A extending from first neck 106A engages or abuts against the floor of recess 112B formed in neck 106B, thereby preventing first jaw 104A from twisting about second jaw 104B and becoming out of plane with one another. It follows that, tongues 110A and 110B in cooperation with recesses 112B and 112A, respectively, will prevent deflection forces acting directly on second jaw 104B from twisting second jaw 104B about first jaw 104A thereby preventing jaws 104A and 104B from becoming out of plane with one another. This can be especially advantageous when arms 102A and 102B are not joined at their proximal ends. It is apparent that inter-leg engaging members also prevent jaws 104A and 104B from becoming out of plane with one another when a force is applied in either direction "A" or direction "B" to second jaw 104B as well.

Jaw blade 100, according to the present disclosure, is fabricated of a material having sufficient resilience such that clamping of the pair of jaws 104A and 104B toward each other to close a clip therebetween will be followed by a return of the jaws 104A and 104B to their original position upon release of the clamping forces. However, unlike the prior art jaw blades, the jaw blade according to the present disclosure is less susceptible to the effects of torsional or bending forces acting thereon as a result of one or more inter-leg engaging members, here shown as a pair of arms 108A and 108B that extend preferably from corresponding neck portions 106A and 106B, respectively, and that inter-engage with opposed neck portions 106B and 106A, respectively, thereby reducing distortion and maintaining or reducing the loss of co-planarity.

Figure 4:
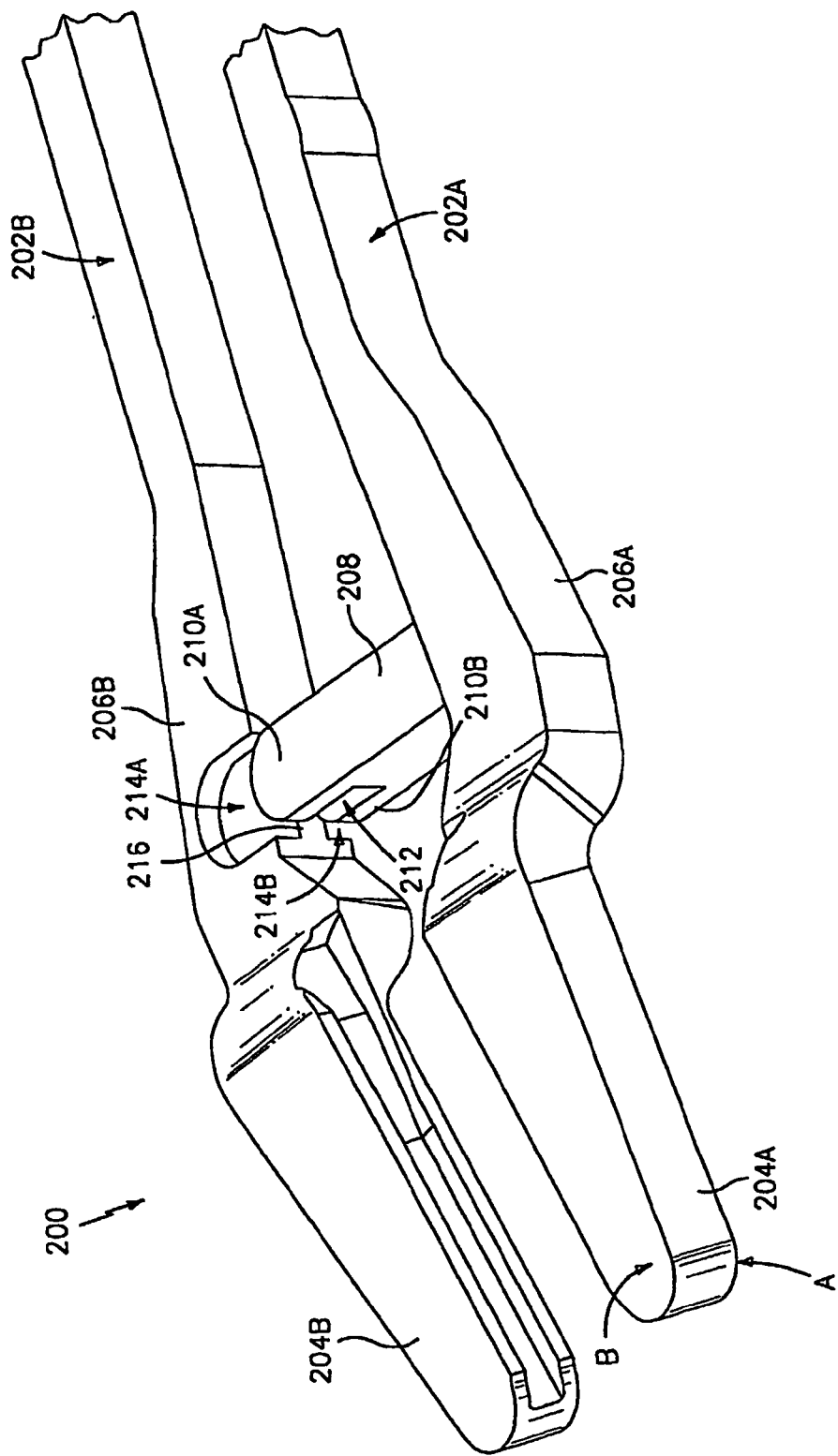
FIG. 4 is an enlarged perspective view, with portions broken away, of a distal end of a jaw mechanism according to an alternative embodiment of the present disclosure.
Figure 5:
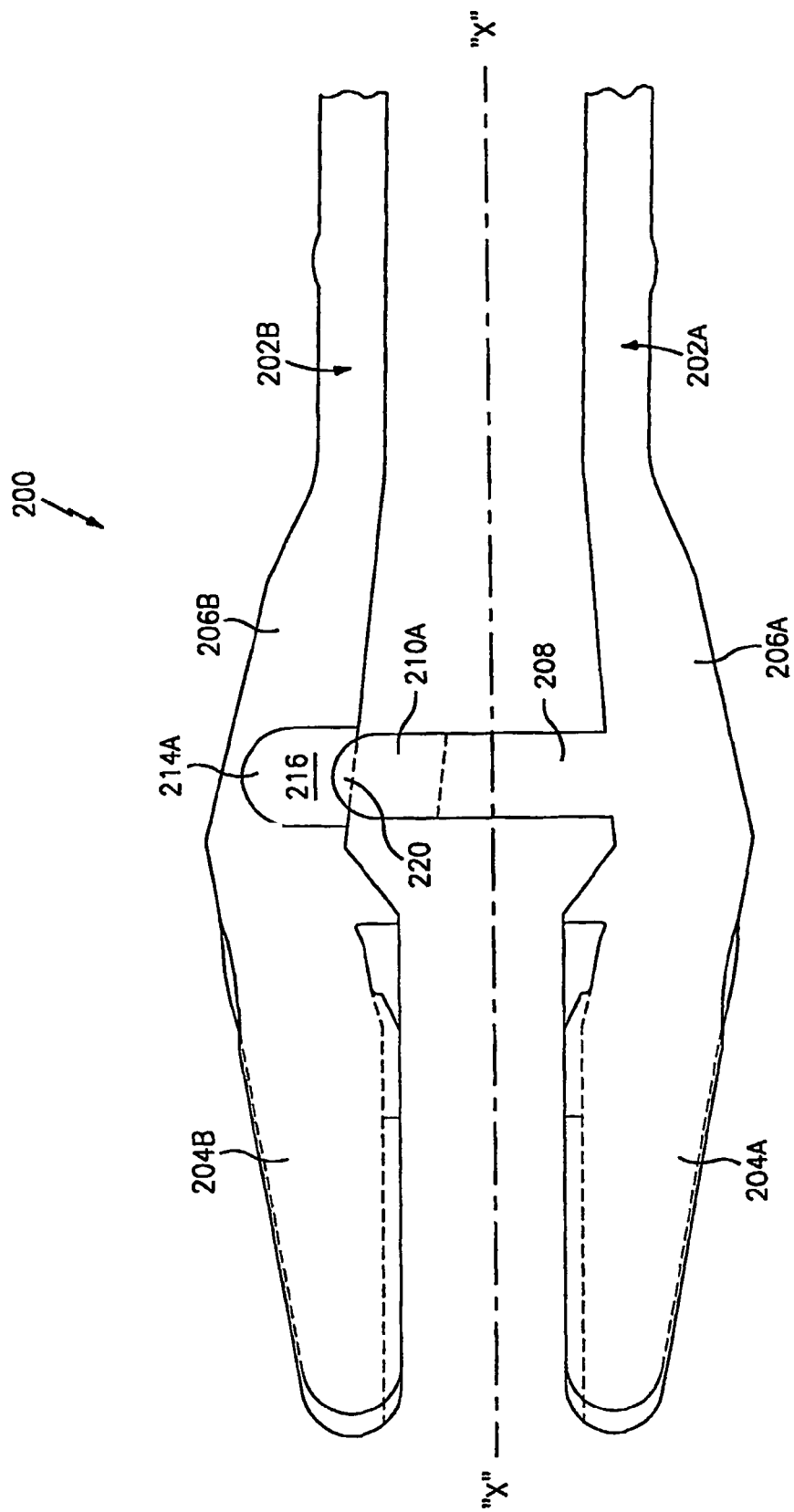
FIG. 5 is a top plan view, with portions broken away, of the distal end of the jaw mechanism shown in FIG. 4.

FIGS. 4 and 5 show the distal end portion of an alternative jaw blade, generally designated 200, in accordance with the present disclosure for use in connection with the surgical clip applier 10. The distal end portion of jaw blade 200 includes a first leg 202A and a second leg 202B each having a corresponding intermediate neck portion 206A, 206B, and a corresponding jaw 204A and 204B formed at a distal end thereof and configured and adapted for receiving a surgical clip (not shown) therebetween. Preferably, legs 202A, 202B are coplanar and together define a plane. As best seen in FIG. 5, jaw blade 200 defines a longitudinal axis "X". Neck portion 206A includes an arm 208 extending therefrom and oriented toward neck portion 206B, which arm 208 includes at its distal end an upper tongue and a lower tongue 210A and 210B, respectively, which together define a clevis 212 therebetween. Neck portion 206B includes upper and lower recesses 214A and 214B, respectively, formed along a top and a bottom surface thereof, which pair of recesses define a wall 216 therebetween. Wall 216 is configured and adapted to be received within clevis 212 of arm 208 and to engage or abut the walls of tongues 210A, 210B that define clevis 212. In this manner, first jaw 204A is operatively coupled to second jaw 204B in accordance with this disclosure.

FIG. 5 is a top plan view of the distal end portion of jaw blade 200 after it is mounted in the distal end of a clip applier (not shown) while it is in an un-crimped or un-squeezed state (i.e., having jaws 204A and 204B in open position, spaced apart from one another). As seen in FIG. 5, while jaws 204A, 204B are in the un-crimped state, arm 208 extends from neck portion 206A a distance sufficient for a portion of its upper tongue 210A to lap, here, to closely overlie, wall 216 and for a portion of its lower tongue 210B to lap, here, underlie, wall 216 at 220. In this manner, first jaw 204A is aligned or co-planar with second jaw 204B at all times from the spaced apart state through to the crimped or closed state. Moreover, by being already lapped, here, closely overlapped and underlapped at 220, while in the open or spaced apart state, jaws 204A and 204B do not have to be at all manipulated, e.g., moved to a more closed position prior to use in order for wall 216 to be aligned and received in clevis 212.

Preferably the lower (or upper) surface of a tongue 210A, 210B overlies (or underlies), and more preferably is slightly engaged with the upper (or lower) surface of the underlying (or overlying) wall 216, preferably when applier 10 is assembled and jaws 204A, 204B are in the fully open position. "Closely overlies (or underlies)" here means that the minimum gap of tongue 210A, 210B above (or below) the upper (or lower) surface of wall 216 is the normal manufacturing tolerance range for applier 10. This can be from about 0.0005 inches to about 0.040 inches or more, the greater the gap, of course, the less effective arm 208 may be in preventing twisting of one jaw or leg relative to the other. The maximum gap, in accordance with this disclosure, is that gap at which, during blunt dissection, the tongue and recess surfaces will engage when a torque is applied to either jaw or leg.

In performing a blunt dissection technique with a clip applier 10 having a jaw blade 200 in accordance with the present disclosure, with assembled jaws 204A, 204B in a fully open position with no surgical clip in place, when a force is applied in direction "A" (directly at or at an angle with respect to the plane defined by legs 202A, 202B) on the first jaw 204A, which force "A" tends to cause the pair of jaws 204A and 204B to twist or bend about one another and become out of plane with one another, the lower tongue 210B, extending from the distal end of arm 208, will engage or abut against the top wall of lower recess 214B (bottom surface of wall 216) formed in neck portion 206B, thereby preventing the first jaw 204A from twisting or bending about the second jaw 204B and from becoming out of plane with one another. Likewise, when a force is applied in a direction "B", opposite to the direction "A", on the first jaw 204A, which force "B" tends to cause the pair of jaws 204A and 204B to twist about one another and become out of plane with one another, upper tongue 210A extending from the distal end of arm 208 will engage or abut against the floor of upper recess 214A (top surface of wall 216) formed in neck portion 206B, thereby preventing the first jaw 204A from twisting about the second jaw 204B and from becoming out of plane with one another. Thus, tongues 210A and 210B, in cooperation with wall 216 dividing recesses 214A and 214B, will prevent forces acting directly on the second jaw 204B from twisting or bending the second jaw 204B about the first jaw 204A, thereby preventing jaws 204A, 204B from coming out of plane with one another.

It is contemplated that jaw configurations in accordance with the present disclosure can be fabricated from any suitable biologically inert material including, but not limited to, engineering plastics, stainless steel, titanium, shape memory alloys and spring steel as well as composites.

The high torque jaws according to the present disclosure can be incorporated in the assembly of new fastener or clip appliers or in the alternative can be a simple low cost modification to existing fastener or clip appliers wherein only the distal end of the jaws, legs of the blades, or the jaw blades, need to be replaced without the need to modify any other portion of the surgical instrument. Stated differently, the high torque jaws according to the present disclosure can be retrofitted into existing fastener or clip appliers.

Figure 6:
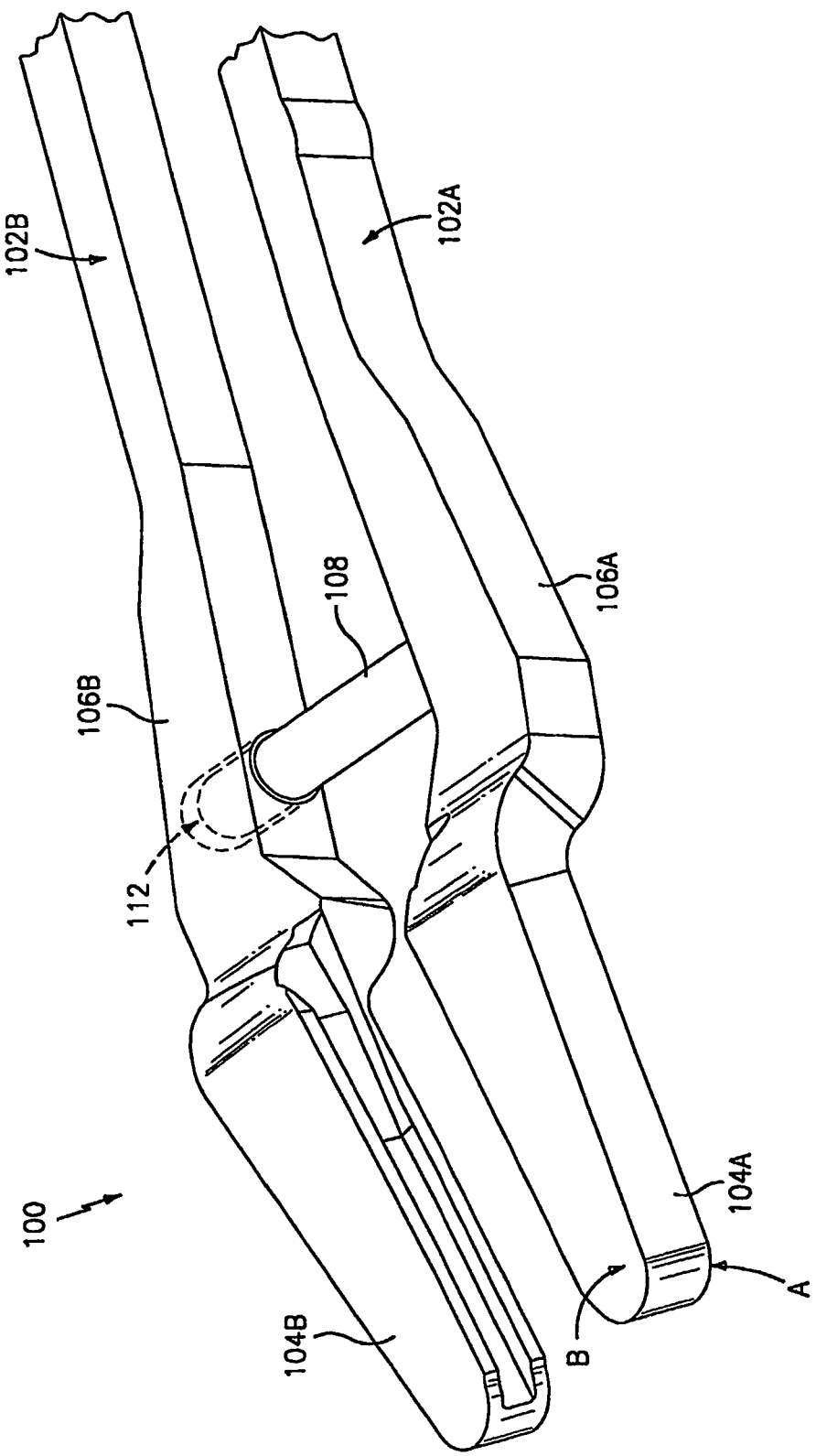
FIG. 6 is an enlarged perspective view, with portions broken away, of a distal end of a jaw mechanism according to a further embodiment of the present disclosure.
Figure 7:
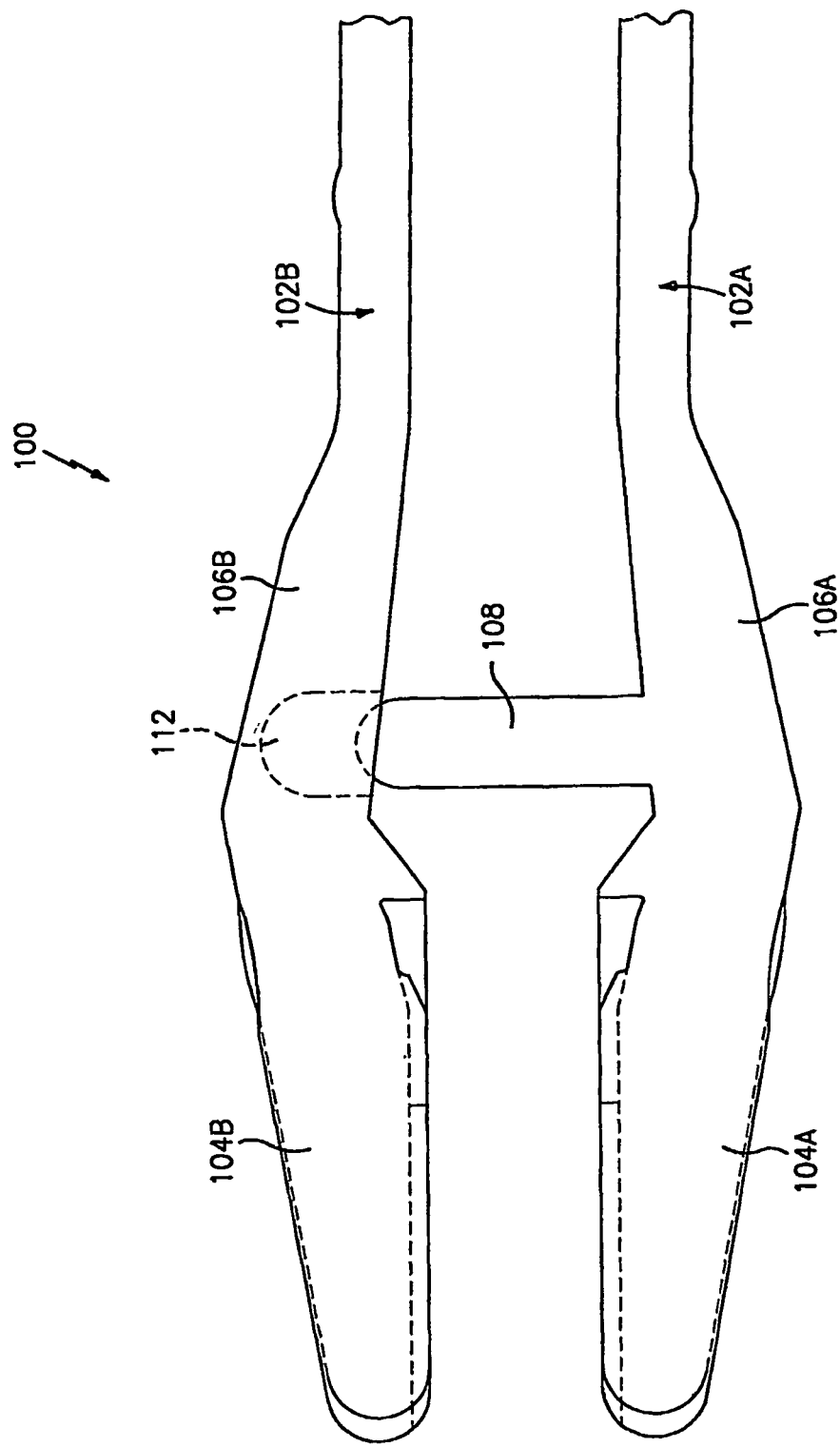
FIG. 7 is a top plan view, with portions broken away, of the distal end of the jaw mechanism shown in FIG. 6.

It is understood that the inter-leg engaging member of the jaw blade of the disclosure is not limited to those disclosed above or shown in the drawings. Rather, the inter-leg engaging member and cooperative receiving structure can, for example, be any suitable male/female arrangement. As seen in FIGS. 6 and 7, an inter-leg engaging member 108 can extend from the inner surface of one of the legs and enter an aperture 112 formed in the inner surface of the juxtaposed leg.

Figure 8:
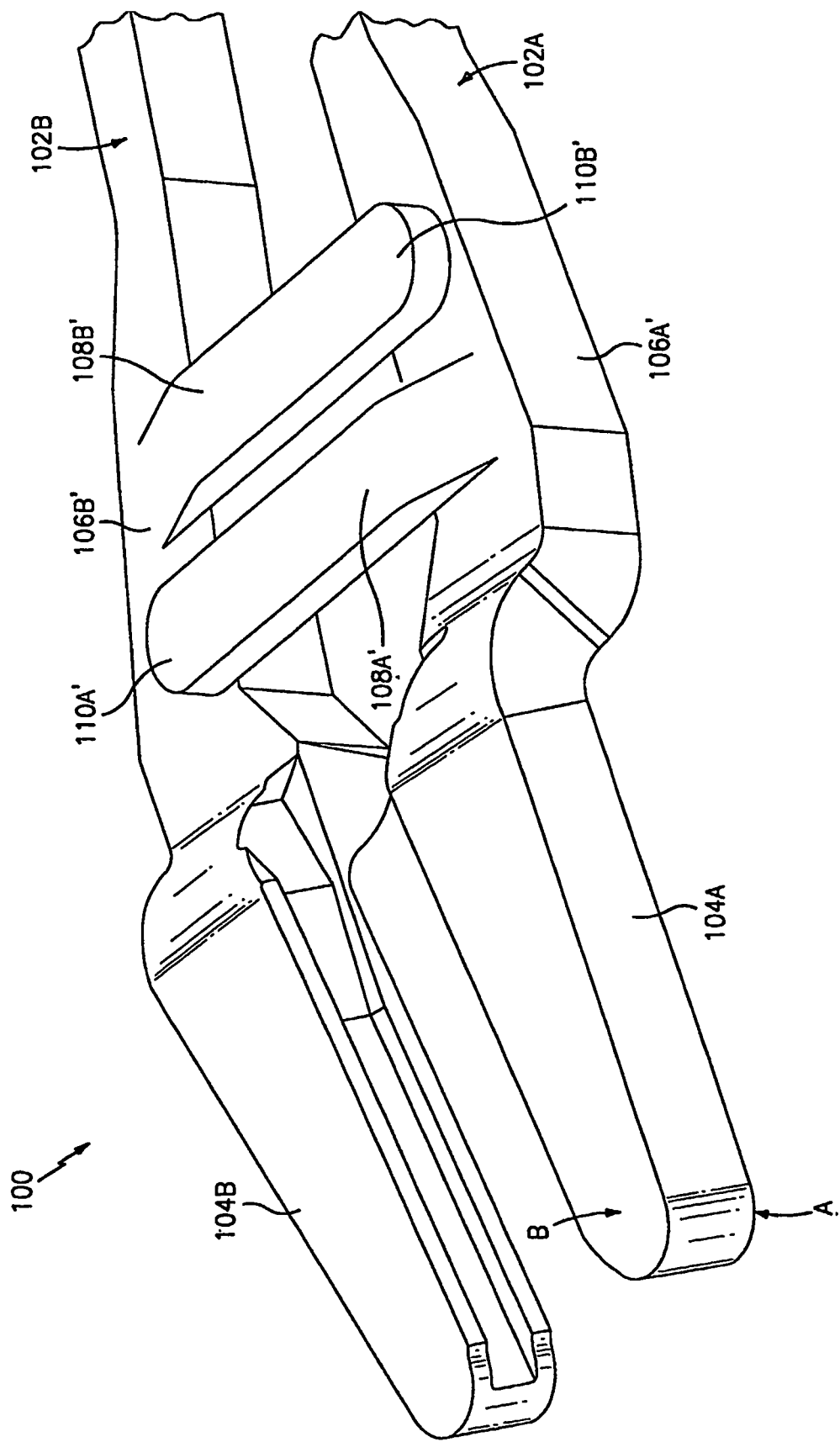
FIG. 8 is an enlarged perspective view, with portions broken away, of a distal end of a jaw mechanism according to yet another embodiment of the present disclosure.

Each of the above disclosed inter-leg engaging members preferably are configured to give the jaw blade a low profile. However, it is envisioned that various other inter-leg engaging members can be provided which tend to reduce the vertical deflection forces acting on each individual leg from causing the pair of legs from coming out of alignment or co-planarity with each other. For example, as seen in FIG. 8, it is envisioned that the inter-leg engaging member can include a first arm 108A' having one end unitary with or fixedly secured to an upper surface of a neck 106A' or other portion of a first leg 102A of a jaw blade and an opposed end or portion 110A' overlying the upper surface of a neck 106A' or other portion of a second leg 102B of the jaw blade, and a second arm 108B' having one end unitary with or fixedly secured to an upper surface of neck 106B' or other portion of second leg 102B of the jaw blade and an opposed end or portion 110B' overlying the upper surface of neck 106A' or other portion of first leg 102A of the jaw blade. In this manner, as one leg is deflected either vertically upward or downward, the first and the second arm cause the second leg to deflect vertically as well.

Figure 9:
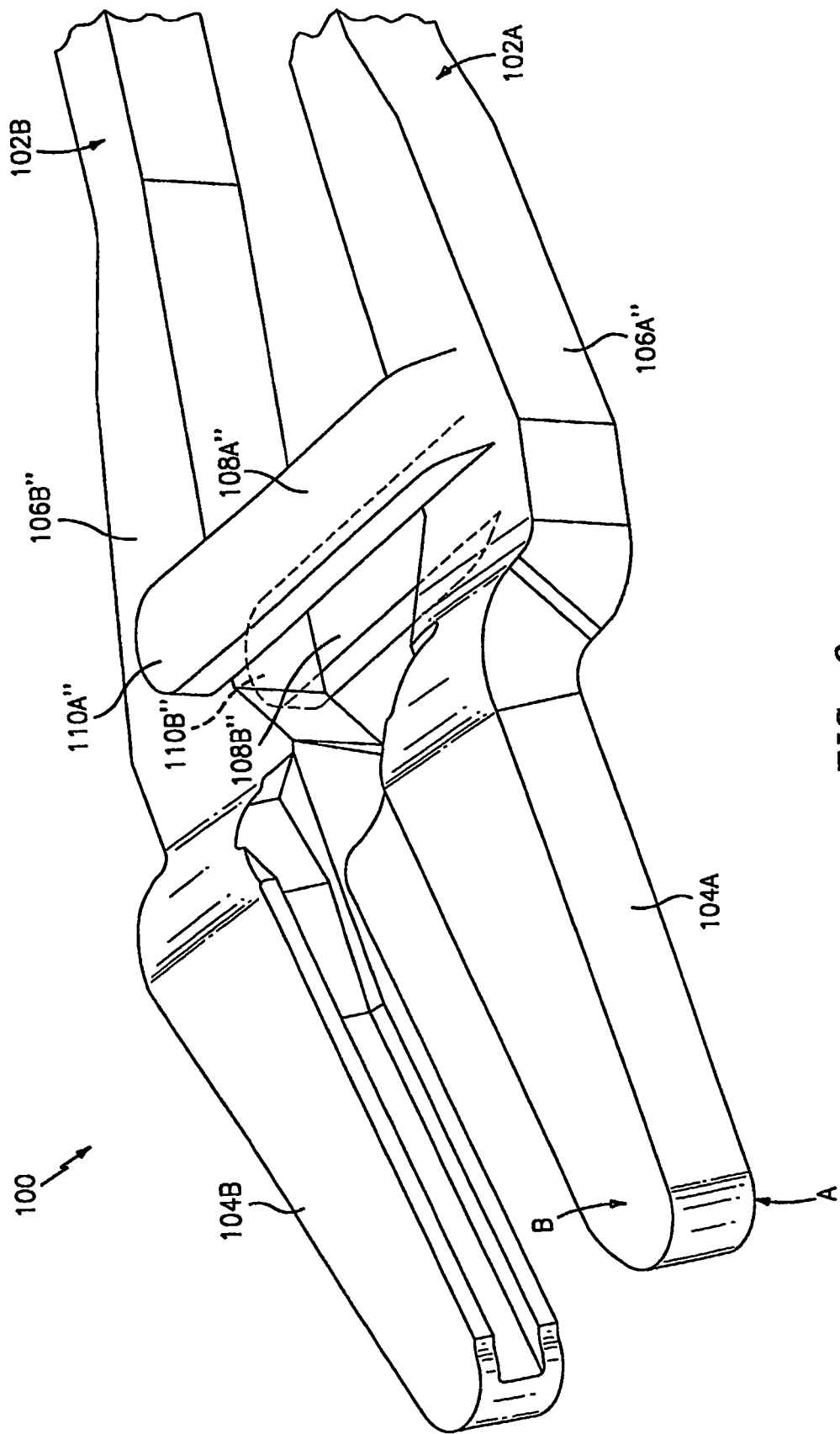
FIG. 9 is an enlarged perspective view, with portions broken away, of a distal end of a jaw mechanism according to a further embodiment of the present disclosure.

By way of a further example, as seen in FIG. 9, it is envisioned that the inter-leg engaging members can include a first arm 108A" having one end unitary with or fixedly secured to an upper surface of a neck 106A" or other portion of a first leg 102A of a jaw blade and an opposed end or portion 110A" overlying an upper surface of a neck 106B" or other portion of a second leg 102B of the jaw blade; and a second arm 108B" having one end unitary with or fixedly secured to a lower surface of neck 106A" or other portion of first leg 102A of the jaw blade and an opposed end 110B" or portion underlying a lower surface of neck 106B" or other portion of second leg 102B of the jaw blade. In this manner, as one leg is deflected either vertically upward or downward, the first and the second arm cause the second leg to deflect vertically as well.

As a further example, each leg can have an inter-leg engaging member, e.g., an arm, extending therefrom and the arms can closely overlie and/or interengage each other, to achieve the objective of the disclosure.

According to an aspect of the present disclosure, it is envisioned, that when the jaw blade is unbiased, the arms of the inter-leg engaging members may not overlie or underlie and/or engage each other or the arms' respective juxtaposed neck portions. The arms may only overlie or underlie and/or engage each other or their respective juxtaposed neck portions when the jaws of the jaw blade are at least partially biased and/or approximated toward one another. It is also envisioned that the arms can be transversely spaced from one another and define a transverse gap therebetween. Accordingly, in these instances for example, the arms of the inter-leg engaging members will first contact and/or engage one another or their respective juxtaposed neck portions and provide advantages of the invention when a vertical and/or a torsional force is applied to either and/or both of the jaws of the jaw blade.

The arm(s) can be any suitable width or diameter and can extend from any portion along the length of the legs, neck or jaw portion of the blade so long as the arm(s) do not interfere with the feeding of the clips into and through the jaws. Generally speaking, the arm(s) are most effective when they are located as close to the distal tip of the jaws as possible, and are decreasingly effective the further they are removed from the distal tip of the jaws. Also generally speaking, to allow for visibility of a clip while seated in the jaw, the arm(s) desirably are located beyond the proximal end, e.g., the backspan, of the seated clip. Thus, for a seated 0.3 inch long clip, the arm(s), would desirably be positioned at least from about 0.3 inches to about 2.0 inches from the distal tip of the jaws.

Although the present disclosure is explained in reference to a clip applier, it is understood that the disclosure applies to apparatus for applying surgical fasteners or clips.

It is understood that various modifications may be made to the embodiments disclosed herein. For example, it is envisioned that the jaws according to the present disclosure can be thickened in the vertical direction, anywhere along the length of the jaws, in order to provide increased rigidity and resistance to vertical deflections. Therefore, the above description should not be construed as limiting, but merely as an exemplification of preferred embodiments. Those skilled in the art will envision other modifications within the scope and spirit of the claims appended hereto.

What is claimed is:

1. A surgical clip applying apparatus, comprising:
   a handle portion including a moveable handle and a stationary hand grip;
   an elongated body portion extending from the handle portion; and
   a jaw blade extending from said elongated body portion and operably connected to the handle portion for selective closure upon, an actuation of the moveable handle, the jaw blade comprising:
      a first leg and a second leg, each leg having a jaw integrally connected thereto and extending distally therefrom, each jaw defining a channel oriented substantially along a respective longitudinal axis thereof, wherein the channels are configured to receive a surgical clip therebetween, wherein each jaw is oriented at an angle with respect to a plane defined by the first and second leg; and
      an inter-leg engaging member extending from each of the first and second legs and including a distal end engageable with the other of the first and second legs, wherein the distal end of each inter-leg engaging member is at all times at least partially engaged with the other of the first and second legs.

2. The apparatus of claim 1, wherein when the at least one inter-leg engaging member is engaged with the other of the first and second legs, a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

3. The apparatus of claim 1, wherein the jaw blade includes two inter-leg engaging members, a first inter-leg engaging member that extends from the first leg and is engageable with the second leg, and a second inter-leg engaging member that extends from the second leg and is engageable with the first leg.

4. The apparatus of claim 3, wherein when the respective first and second inter-leg engaging members are engaged with the respective second and first legs, a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

5. The apparatus of claim 3, wherein the first inter-leg engaging member comprises a first arm configured and adapted to engage the second leg, and the second inter-leg engaging member comprises a second arm configured and adapted to engage the first leg.

6. The apparatus of claim 3, wherein when the jaws of the jaw blade are in an open position, a portion of the inter-leg engaging member that extends from one of the first and second legs, slidingly engages a portion of the other of the first and second legs.

7. The apparatus of claim 1, wherein the first leg includes an inner surface oriented toward the second leg and a recess formed in an upper portion of the inner surface of the first leg, and the second leg includes an inner surface oriented toward the first leg and a recess formed in an upper portion of the inner surface of the second leg, the inner surface of the first leg having a first inter-leg engaging member comprised of a first arm that includes a tongue extending distally therefrom, the tongue of the first arm being configured and dimensioned to be received in and being engageable with the recess in the upper portion of the second leg, and the inner surface of the second leg having a second inter-leg engaging member comprised of a second arm that includes a tongue extending distally therefrom, the tongue extending from the second arm being configured and dimensioned to be received in and being engageable with the recess in the upper portion of the first leg.

8. The apparatus of claim 7, wherein a portion of the tongue of the first arm closely overlies the recess in the second upper surface of the second leg, and a portion of the tongue of the second arm closely underlies the recess in the first lower surface of the first leg.

9. The apparatus of claim 1, wherein there are two inter-leg engaging members, a first inter-leg engaging member comprising a first arm that extends from the first leg and closely overlies and is engageable with the second leg, and a second inter-leg engaging member comprising a second arm that extends from the first leg and closely underlies and is engageable with the second leg.

10. The apparatus of claim 1, wherein the first leg includes a first arm that extends from the first leg toward the second leg, the first arm including a pair of transversely spaced apart tongues extending distally therefrom, the second leg including an upper and lower surface, an upper recess in the upper surface thereof, and a lower recess in the lower surface thereof, wherein the pair of spaced apart tongues of the first arm are configured and dimensioned to be received in and be engageable with the upper and lower recesses formed respectively in the upper and lower surfaces of the second leg.

11. The apparatus of claim 10, wherein the pair of spaced apart tongues of the first arm closely overlie and underlie the respective upper and lower recesses of the second leg.

12. The apparatus of claim 1, wherein when the jaws of the jaw blade are in an open position, a portion of the inter-leg engaging member that extends from one of the first and second legs, closely overlies a portion of the other of the first and second legs.

13. The apparatus of claim 1, wherein each of the first and second legs includes a neck adjacent the jaw of the respective first and second legs, and the inter-leg engaging member extends from one of the necks.

14. The apparatus of claim 13, wherein there are two inter-leg engaging members, one that extends from the neck, of the first leg, and another that extends from the neck of the second leg.

15. A surgical clip applying apparatus, comprising:
a handle portion including a moveable handle;
an elongated body portion rotatably mounted to and extending from the handle portion; and
a jaw blade for use in a surgical clip applier, wherein the jaw blade is selectively closed upon an actuation of the moveable handle, the jaw blade comprising:
a first leg and a second leg, each leg having a jaw integrally connected thereto, and extending distally therefrom, each jaw defining a channel oriented substantially along a respective longitudinal axis thereof, wherein the channels are configured to receive a surgical clip therefrom; and
at least one inter-leg engaging member extending from one of the first and second legs, and extending between and engaged with the other of the first and second legs, wherein rotation of the elongated body portion relative to the handle portion causes rotation of the jaw blade.

16. The apparatus of claim 15, wherein when the at least one inter-leg engaging member is slidingly engaged with the other of the first and second legs, such that a vertical displacement in a first direction of one of the first and second legs causes a first corresponding displacement in the first direction of the other of the first and second legs, and such that a vertical displacement in a second direction, opposite the first direction, of the one of the first and second legs causes a second corresponding displacement in the second direction of the other of the first and second legs.

17. The apparatus of claim 15, wherein the first leg includes a first neck portion and the second leg includes a second neck portion, the first and second neck portions adjoining the first and second jaws, and the at feast one inter-leg engaging member including:
a first arm that extends from the first neck portion and slidingly engages the second neck portion; and
a second arm, spaced from the first arm, that extends from the second neck portion and slidingly engages the first neck portion.

18. The apparatus according to claim 17, wherein the first neck portion includes a first inner surface oriented toward the second neck portion and a recess formed in a lower portion of the first inner surface, and the second neck portion includes a second inner surface oriented toward the first neck portion and a recess formed in a lower portion of the second inner surface;
wherein the first arm extending from the first inner surface of the first neck portion includes a tongue extending distally therefrom, the tongue extending from the first arm being configured and adapted to be received in the recess formed in the lower portion of the second neck portion; and
wherein the second arm extending from the second inner surface of the second neck portion includes a tongue extending distally therefrom, the tongue extending from the second arm being configured and adapted to be received in the recess formed in the lower portion of the first neck, portion, wherein at least one of the first and second tongues is slidingly engaged with its respective recess.

19. The apparatus according to claim 17, wherein the at least one inter-leg engaging member comprises:
a first arm configured and adapted to extend from the first neck portion and overlie and slidingly engage the second neck portion; and
a second arm configured and adapted to extend from the first neck portion and underlie and slidingly engage the second neck portion.

20. The apparatus according to claim 17, wherein the at least one inter-leg engaging member comprises:
a first arm configured and adapted to extend from the first neck portion and overlie and slidingly engage the second neck portion; and
a second arm configured and adapted to extend from, the second neck portion and overlie and slidingly engage the first neck portion.

21. The apparatus according to claim 17, wherein the jaw blade defines a longitudinal axis, and wherein the first neck portion includes an arm extending therefrom and substantially toward the second neck portion, the arm including a pair of spaced apart tongues extending at an angle to the longitudinal axis of the jaw blade, wherein the second neck portion includes a recess formed in each of the upper and lower surface thereof, and wherein the pair of spaced apart tongues of the arm respectively slidingly engage the recesses formed in the upper and lower surfaces of the second neck portion.

22. An apparatus for applying surgical fasteners or clips, the apparatus comprising:
a handle portion including a moveable handle,
a body portion extending from the handle portion and including a rotating collar for rotating the body portion relative to the handle portion, and
a jaw blade extending from the body portion at an end opposite the handle portion and being selectively closed upon an actuation of the moveable handle, wherein rotation of the body portion relative to the handle portion causes rotation of the jaw blade, the jaw blade having a first leg and a second leg, each leg having a jaw integrally connected thereto, each jaw defining a channel oriented substantially along a respective longitudinal axis thereof, wherein the channels are configured to receive a fastener or clip, a the jaw blade being movable between an open position for receiving the fastener or clip and a closed position for forming the fastener or clip in response to a movement of the handle portion; and a fastener or clip supply disposed within the body portion, wherein the jaw blade further includes at least one inter-leg engaging member extending between and being adapted to effect an engagement between the first and second legs, wherein vertical displacement in a first direction of one of the first and second legs causes a corresponding displacement in the first direction of the other of the first and second legs, and wherein a vertical displacement in a second direction, opposite the first direction, of one of the first and second legs causes a second corresponding displacement in the second direction of the other of the first and second legs, wherein the jaws are configured to form a surgical clip disposed therebetween.

23. The apparatus of claim 22, wherein the at least one inter-leg engaging member is adapted to effect engagement when the jaws are in an open position.

24. The apparatus of claim 22, wherein the at least one inter-leg engaging member is adapted to effect engagement when the jaws are in a closed position.

25. A method for applying surgical clips and performing blunt dissection of tissue, comprising the steps of:

providing a surgical clip applier for applying surgical clips, which surgical clip applier includes:

a handle portion including a moveable handle;

an elongated body portion rotatably mounted to and extending from the handle portion; and a jaw blade supported on a distal end of the elongated body and being selectively closed upon an actuation of the moveable handle, wherein rotation of the elongated body portion relative to the handle portion causes rotation of the jaw blade, the jaw blade having:

a first leg and a second leg, each of the first and second legs having a jaw integrally connected thereto and extending distally therefrom, each jaw defining a Channel oriented substantially along a respective longitudinal axis thereof, wherein the channels are configured to receive the surgical clip therebetween; and at least one inter-leg engaging member extending between and effecting an engagement between the first and second legs, such that a vertical displacement in a first direction of one of the first and second legs causes a first corresponding displacement in the first direction of the other of the first and second legs, and such that a vertical displacement in a second direction, opposite the first direction, of one of the first and second legs causes a second corresponding displacement in the second direction of the other of the first and second legs; and performing a blunt dissection technique utilizing the jaws of the clip applier; and applying a surgical clip to a tissue or vascular target area utilizing the clip applier.

26. A surgical clip applier, comprising:

a handle portion including a movable handle;

an elongated body portion extending from the handle portion and including a rotating collar for rotating the body portion relative to the handle portion; and a jaw blade supported on a distal end of the elongated body and being selectively closed upon an actuation of the moveable handle, wherein rotation of the elongated body portion relative to the handle portion causes rotation of the jaw blade, the jaw blade comprising:

a first leg;

a second leg spaced from and parallel to the first leg, the first and second legs defining a plane, each leg including a jaw integrally formed at a distal end thereof and extending distally therefrom, each jaw defining a channel oriented substantially along a respective longitudinal axis thereof wherein the channels are configured to receive a surgical clip therebetween; and at least one inter-leg engaging member extending between the first and the second legs and operatively engaged therewith, wherein the at least one inter-leg engaging member maintains or reduces the loss of co-planarity of the first leg with respect to the second leg.

27. The apparatus according to claim 26, wherein the operative engagement of the at least one inter-leg engaging member causes the first and second leg members to deflect and maintain their co-planarity when one of the first and second legs is deflected in a direction which is orthogonal with respect to the plane defined by the first and second legs.

28. The apparatus according to claim 27, wherein the jaw blade includes:

a first inter-leg engaging member integrally formed with the first leg and extending substantially toward the second leg, the first inter-leg engaging member including a tongue extending from a distal end thereof, which tongue is configured and dimensioned to interengage a recess formed in a surface of the second leg; and a second inter-leg engaging member integrally formed with the second leg and extending substantially toward the first leg, the second leg inter-engaging member including a tongue extending from a distal end thereof, which tongue is configured and dimensioned to interengage a recess formed in a surface of the first leg.

29. The apparatus according to claim 28, wherein the recess formed in the second leg is formed in one of a top and a bottom surface thereof, and wherein the recess formed in the first leg is formed in one of a top and a bottom surface thereof, which recess formed in the first leg is formed in the surface opposite the top and bottom surface in which the recess of the second leg is formed.

30. The apparatus according to claim 27, wherein the at least one inter-leg engaging member includes a single inter-leg engaging member integrally formed with one of the first and second legs and extending substantially toward the other of the first and second legs, the inter-leg engaging member including a pair of tongues extending from a distal end of the inter-leg engaging member and spaced from one another in a direction orthogonal to the plane defined by the first and second legs, each tongue of the pair of tongues being configured and dimensioned to interengage a respective recess formed in a top surface and a bottom surface of the second leg.

* * * * *